United States Patent [19]

Jary et al.

[11] 4,304,734

[45] Dec. 8, 1981

[54] 6-AMINO-1-HYDROXYHEXYLIDENE DIPHOSPHONIC ACID, SALTS AND A PROCESS FOR PRODUCTION THEREOF

[75] Inventors: Jiri Jary; Veroslava Rihakova; Alena Zobacova, all of Prague, Czechoslovakia

[73] Assignee: Vysoka skola chemicko-technologicka, Prague, Czechoslovakia

[21] Appl. No.: 197,608

[22] Filed: Oct. 16, 1980

[51] Int. Cl.³ ................................................ C07F 9/38
[52] U.S. Cl. ................................................ 260/502.5
[58] Field of Search ..................................... 260/502.5

[56] References Cited

U.S. PATENT DOCUMENTS 3,812,221  5/1974  Braden et al. ............... 260/502.5
4,054,598  10/1977  Blum et al. ................. 260/502.5
4,239,695  12/1980  Chai et al. .................. 260/502.5

*Primary Examiner*—Joseph E. Evans

[57] ABSTRACT

6-amino-1-hydroxyhexylidene diphosphonic acid (I), salts of acid (I), and a process for the production thereof. Acid (I) has the summary formula

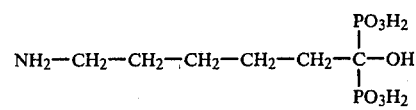

Acid (I) and its salts are useful for pharmocologial purposes.

In the production of acid (I) a mixture of phosphorous acid and phosphorous trichloride is reacted with the ε-aminocaproic acid or amide derived therefrom at a temperature from 50° to 150° C. The reaction can be carried out in the presence of an organic solvent, preferably chlorobenzene. Salt of the acid is produced by neutralization with one or two molecular equivalents of alkaline hydroxide, preferably sodium hydroxide.

3 Claims, No Drawings

6-AMINO-1-HYDROXYHEXYLIDENE DIPHOSPHONIC ACID, SALTS AND A PROCESS FOR PRODUCTION THEREOF

This invention relates to 6-amino-1-hydroxyhexylidene diphosphonic acid, salts thereof and to a process of their production. The acid and salts according to the invention are capable of regulating metal cations content (especially calcium content) in human organism thus enabling to cure diseases connected with content and circulation of these cations in organism. Thus, they prevent tartar formation, inhibit calcification of aorta and kidneys, retard bone decalcification etc. Complexes with radioactive cations can be used for diagnostic purposes. The acid and salts intensify bactericide effect of phenolic compounds. Considering their complex-formative properties and ability to dissolve water unsoluble salts in nonstoiechiometric amounts they can be used wherever it is necessary to prevent sediment or deposit formation.

Mostly non-substituted acids of the general formula

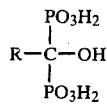

where R signifies alkyl or aryl, are described in the literature.

Besides compounds with a linear chain where R is methyl to heptadecyl, there are also described compounds with a branched chain. Ethylidenehydroxy diphosphonic acid is the most known representative of these compounds. There are available a number of methods for their production, the common feature of which is that the aliphatic acid or its proper derivative is subjected to reaction with phosphorous acid or with its precursor. It is thus possible to allow the acylating agent/chloride or anhydride to react with phosphorous acid or to heat a mixture of aliphatic acid and $P_2O_5$ with phosphorous acid, or optionally to let the corresponding acid react with $PCl_3$ in a proper molar ratio.

Preparation of substituted alkylidenehydroxy diphosphonic acids is, however, more difficult, because substituted aliphatic acids are often subjected to other reactions under similar reaction conditions. An attempt to prepare some amino-derivatives from ethylenediamino tetraacetic acid was thus unsuccessful for splitting of carboxyl and its substitution took place. Furthermore, product isolation with amino acids is difficult, because it is impossible to use distillation for the separation of the reaction mixture; the starting compound, its reaction products, and their esters are not volatile. There have nevertheless been described several lower aminohydroxyalkyliden diphosphonic acids and their N-alkyl derivatives with at most a $C_4$ chain. These acids have an extremely weakly basic amino group, and give neutral salts with two equivalents of sodium hydroxide due to the presence of both phosphonic groups. The neutral salts are thus characterized by a high content of sodium or other metal, which can hamper its use for pharmacological purposes.

The above disadvantages are overcome by the 6-amino-1-hydroxyhexylidene diphosphonic acid of the summary formula (I)

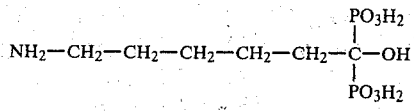

and salts thereof according to the invention.

The invention also includes a process for the production of the acid. In such process a mixture of phosphorous acid and phosphorus trichloride is reacted with the ε-aminocaproic acid or amide derived therefrom at a temperature of 50° to 150° C. The reaction can be carried out in the presence of an organic solvent, preferably chlorobenzene.

The salt of the acid according to the invention is produced in such a way the acid is neutralized with one or two equivalents of alkaline hydroxide, preferably sodium hydroxide.

The new phosphonic acid according to the invention has a character and basicity of amino group which depend upon its distance from acid groups. It forms neutral mono-sodium and alkaline di-sodium salt.

The process for production according to the invention consists in that the ε-aminocaproic acid is transferred to the acid (I) under the effect of phosphorous acid and phosphorous trichloride in the presence of or without an organic solvent; mono- or di-sodium salt of the acid (I) is prepared by neutralization with hydroxide. Instead of the ε-aminocaproic acid its cyclic or linear amide/caprolactam, polyamide/can be used which is hydrolyzed during the reaction.

In the preferred manner of carrying out the process, a mixture of the ε-aminocaproic acid, phosphorous acid and an aprotic solvent is heated to 100° C. and phosphorous trichloride is added dropwise to this mixture while the mixture is stirred. Instead of phosphorous acid, it is possible to use phosphorous trichloride and an adequate amount of water, from which phosphorous acid originates directly in the reaction mixture. This possibility is less advantageous because with it a large amount of hydrogen chloride is liberated. Hydrocarbons or halogenated hydrocarbons, preferably chlorobenzene, are suitable as a solvent. The reaction mixture is heated to 100° C. after mixing of all the components for two to three hours, and the separated solid product is recrystallized from hot water.

A further fraction can be obtained from mother liquors by adding methanol. The pure acid dissolves in water with difficulty; its di-sodium salt is prepared by dissolving the acid in approximately a molecular equivalent amount of sodium hydroxide and by subsequent titration, or by adding exactly two molecular equivalent amounts of sodium hydroxide to a suspension of pure acid in water. The mono-sodium salt is prepared either by adding an equivalent of sodium hydroxide to a suspension of the acid in water, or by neutralization of this suspension with sodium hydroxide to pH=7.

The invention is further explained by the following specific examples.

EXAMPLE 1

A mixture of 13 g ε-aminocaproic acid and 12.7 g phosphorous acid in 100 ml chlorobenzene was heated under stirring to 100° C., and 14 ml of phosphorous trichloride was added dropwise to it within a period of 30 minutes. The solution was then heated under stirring for 3 more hours; insoluble solid matter separated during this time. The solvent was poured off after cooling, the residue was boiled with 60 ml of water for about 30 minutes and subjected to hot filtration with activated charcoal through a layer of supercel. Activated charcoal and supercel were washed with hot water, and the united solids were concentrated at 40° C. in vacuum. Separated crystals were filtered off, and a further fraction was obtained from the mother liquors by adding methanol in excess. Altogether 15 g/55%/of the crystalline acid (I) was obtained; such acid had a melting point of 245° C., absorption in the IR spectrum at 3.15, 6.15 and 6.45μ. The composition of $C_6H_{17}NO_7P_2$/molecular weight 277.2/was calculated to be by weight: 26.00% C, 6.18% H, 5.05% N and found: 26.28% C, 6.45% H, 4.87% N.

EXAMPLE 2

Preparation of mon-sodium salt of acid (I).

2.77 g of the acid in 50 ml water was neutralized by the addition of 10 ml 1 N NaOH; the solution was filtered and concentrated. The separated mono-sodium salt of acid (I) was filtered off, washed with methanol and dried in vacuum.

EXAMPLE 3

Preparation of di-sodium salt of acid (I).

2.77 g of acid (I) was neutralized with 20 ml 1 N NaOH as in Example 2, and the solution was drawn off. The separated di-sodium salt of acid (I) was dried in vacuum.

Although the invention is illustrated and described with reference to a plurality of preferred embodiments thereof, it is to be expressly understood that it is in no way limited to the disclosure of such preferred embodiments, but is capable of numerous modifications within the scope of the appended claims.

We claim:

1. 6-amino-1-hydroxyhexylidene diphosphonic acid of the summary formula (I)

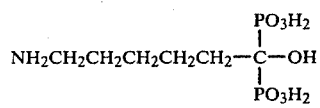

2. The mono-sodium salt of acid (I) according to claim 1.

3. The di-sodium salt of acid (I) according to claim 1.

Notice of Adverse Decision in Interference

In Interference No. 100,890, involving Patent No. 4,304,734, J. Jary, V. Rihakova and A. Zobacova, 6-AMINO-1-HYDROXYHEXYLIDENE DIPHOSPHONIC ACID, SALTS AND A PROCESS FOR PRODUCTION THEREOF, final judgment adverse to the patentees was rendered Dec. 1, 1982, as to claim 1.

[*Official Gazette May 17, 1983.*]